United States Patent
Kishine et al.

(10) Patent No.: US 6,191,233 B1
(45) Date of Patent: Feb. 20, 2001

(54) FLUORINATED TRIALLYL ISOCYANURATES, VULCANIZABLE ELASTOMER COMPOSITIONS CONTAINING THE SAME, AND METHOD FOR VULCANIZATION

(75) Inventors: Mitsuru Kishine; Yutaka Ueta; Yoshiko Mori, all of Settsu; Satoshi Oishi; Katsuhiko Iseki, both of Tsukuba; Yasuji Iwasaki, Settsu, all of (JP)

(73) Assignee: Daikin Industries Ltd., Osaka (JP)

( * ) Notice: Under 35 U.S.C. 154(b), the term of this patent shall be extended for 0 days.

(21) Appl. No.: 09/202,919

(22) PCT Filed: Jun. 30, 1997

(86) PCT No.: PCT/JP97/02253

§ 371 Date: Dec. 23, 1998

§ 102(e) Date: Dec. 23, 1998

(87) PCT Pub. No.: WO98/00407

PCT Pub. Date: Jan. 8, 1998

(30) Foreign Application Priority Data

Jul. 1, 1996 (JP) .................................................. 8-170953

(51) Int. Cl.⁷ .......................... C08F 226/06; C08F 114/20
(52) U.S. Cl. ....................... 525/326.3; 526/248; 526/261; 522/167
(58) Field of Search .......................... 525/326.3; 526/248, 526/261; 522/167

(56) References Cited

U.S. PATENT DOCUMENTS

| 4,211,868 | 7/1980 | Erdman | 544/221 |
| 4,320,216 | 3/1982 | Apotheker | 526/248 |

FOREIGN PATENT DOCUMENTS 3020185  12/1980  (DE) .

*Primary Examiner*—James J. Seidleck
*Assistant Examiner*—Olga Asinossky
(74) *Attorney, Agent, or Firm*—Birch, Stewart, Kolasch & Birch, LLP

(57) ABSTRACT

A fluorine-containing triallyl isocyanurate of the formula [I]:

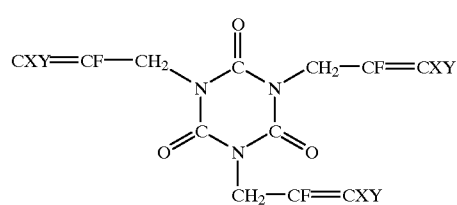

wherein at least one of X and Y is a fluorine atom, and the other is a hydrogen atom or a fluorine atom, exhibits good curing properties even when it is used as a crosslinking aid for elastomers which are required to have good heat resistance, such as in particular, fluororubbers, and provides cured materials having good mechanical properties and heat resistance.

18 Claims, No Drawings

FLUORINATED TRIALLYL ISOCYANURATES, VULCANIZABLE ELASTOMER COMPOSITIONS CONTAINING THE SAME, AND METHOD FOR VULCANIZATION

This application is the national phase under 35 U.S.C. §371 of prior PCT International Application No. PCT/JP97/02253 which has an International filing date of Jun. 30, 1997 which designated the United States of America.

FIELD OF THE INVENTION

The present invention relates to a fluorine-containing triallyl isocyanurate, a curing agent comprising a fluorine-containing triallyl isocyanurate, a curable elastomer composition comprising such a curing agent, and a method for the curing of such a composition.

PRIOR ART

Triallyl isocyanurate (hereinafter referred to as "TAIC") is a symmetric polyfunctional triazine compound, and used as a reactive monomer, a crosslinking agent of various synthetic resins and synthetic rubbers, a crosslinking aid, and a modifier.

TAIC can greatly improve the heat resistance, mechanical properties, weather resistance, hydrolysis resistance, etc. of various polymer, by making effective use of good heat resistance of a triazine ring which forms a core structure of TAIC.

For example, when TAIC is used as a crosslinking aid in the peroxide curing of fluororubbers which are required to have very high heat resistance, it achieves high advantages that the fluororubbers can be very effectively cured, and the obtained cured materials have good mechanical properties. However, the heat resistance of the cured materials is not always satisfactory in comparison with the heat resistance of cured materials which are cured by other curing systems such as a polyol or polyamine curing system. Thus, it is desired to improve the heat resistance of cured materials of fluororubbers obtained by peroxide curing.

A proposal is made in U.S. Pat. No. 4,320,216 to replace a part of hydrogen atoms in the three allyl groups of TAIC with a fluorine atom which improves heat resistance. However, this U.S. patent describes the use of such a fluorine-substituted TAIC as a modifier to obtain gelled fluororubbers by copolymerization.

Klenovich, S. V. et al describe, in Zh. Prikl, Khim. (Leningrad) (1987), 60(3), 656–8, 1,3,5-tris(2-fluoro-2-propenyl)-1,3,5-triazine-2,4,6-trione, which is a derivative of TAIC in which a part of hydrogen atoms in the three allyl groups of TAIC are replaced with fluorine atoms which improve heat resistance. However, this literature reports only that the replacement of a hydrogen atom at the 2-position of an allyl group retards the transfer from TAIC, but does not describe the use of such a compound as a crosslinking aid for fluororubbers.

PROBLEMS TO BE SOLVED BY THE INVENTION

The present invention intends to provide a derivative of TAIC, which has very good curing properties when used as a crosslinking aid for fluororubbers which are required to have high heat resistance, and which is useful as a crosslinking aid that can provide a cured material having excellent mechanical properties and also heat resistance.

MEANS TO SOLVE THE PROBLEMS

According to the first aspect, the present invention provides a fluorine-containing triallyl isocyanurate of the formula [I]:

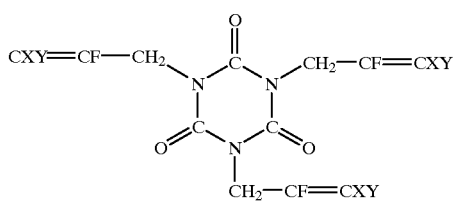

wherein at least one of X and Y is a fluorine atom, and the other is a hydrogen atom or a fluorine atom.

According to the second aspect, the present invention provides a crosslinking aid comprising a fluorine-containing triallyl isocyanurate of the formula [II]:

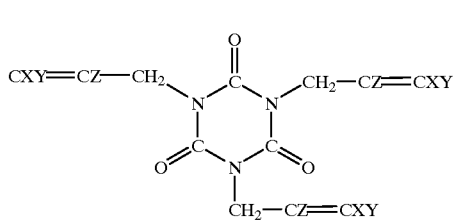

wherein at least one of X, Y and Z is a fluorine atom, and the others are hydrogen or fluorine atoms.

According to the third aspect, the present invention provide a curable elastomer composition comprising a peroxide-curable elastomer, a fluorine-containing triallyl isocyanurate of the above formula [I] or [II] as a crosslinking aid, and an organic peroxide.

According to the fourth aspect, the present invention provides a method for the curing of a peroxide-curable elastomer comprising curing such an elastomer with an organic peroxide in the presence of a fluorine-containing triallyl isocyanurate of the above formula [I] or [II] as a crosslinking aid.

According to the fifth aspect, the present invention provides a shaped article, in particular, a sealing material, obtained by shaping the curable elastomer composition of the present invention.

One of the reasons for the low heat resistance of the organic peroxide-cured materials of fluororubbers using conventional fluorine-free triallyl isocyanurate may be the insufficient heat resistance of bonds (crosslinked sites) between the fluororubbers and the crosslinking aid. It may be assumed that the introduction of a fluorine atom or fluorine atoms into the allyl groups of TAIC can improve the heat resistance of crosslinked sites.

The fluorine-containing triallyl isocyanurate of the present invention can be prepared from a corresponding starting material by the same method as that for the preparation of conventional triallyl isocyanurate.

For example, diethyl azodicarboxylate is dropwise added into a solution of a fluorine-containing allyl alcohol, cyanuric acid and triphenylphosphine in, for example, dimethylacetamide, and stirred at room temperature for several hours. The solvent is evaporated off from the resulting reaction mixture, and the concentrated mixture is purified by silica gel chromatography. The details of such a method will be described in the Examples below.

Preferable examples of the fluorine-containing triallyl isocyanurate of the present invention are 1,3,5-tris(2,3,3-trifluoro-2-propenyl)-1,3,5-triazine-2,4,6-trione, and 1,3,5-tris(2,3-difluoro-2-propenyl)-1,3,5-triazine-2,4,6-trione.

The fluorine-containing triallyl isocyanurate of the present invention is preferably used as a crosslinking aid when elastomers are cured with peroxides. When a fluorine-containing triallyl isocyanurate is used as a crosslinking aid, any known fluorine-containing isocyanurate may be suitably used.

The known fluorine-containing isocyanurates include 1,3,5-tris(2-fluoro-2-propenyl)-1,3,5-triazine-2,4,6-trione, 1,3,5-tris(3-fluoro-2-propenyl)-1,3,5-triazine-2,4,6-trione, 1,3,5-tris(3,3-difluoro-2-propenyl)-1,3,5-triazine-2,4,6-trione, etc.

Elastomers which can be cured using a curing aid comprising the fluorine-containing triallyl isocyanurate of the present invention include the following elastomers which may have the crosslinking site of a halogen atom such as an iodine atom or a bromine atom:

vinylidene fluoride-hexafluoropropylene elastomers, vinylidene fluoride-tetrafluoroethylene-hexafluoropropylene elastomers, vinylidene fluoride-chlorotrifluoroethylene elastomers, tetrafluoroethylene-propylene elastomers, hexafluoropropylene-ethylene elastomers, perfluoro (alkyl vinyl ether)-tetrafluoroethylene elastomers, vinylidene fluoride-tetrafluoroethylene-perfluoro(alkyl vinyl ether) elastomer.

The above fluorine-containing elastomers may contain a copolymerized crosslinking-site monomer of the following formula, in place of or in addition to the crosslinking site of a halogen atom such as an iodine atom or a bromine atom:

$X^1CH_2CF_2CF_2(OCH_2CF_2CF_2)_m(OCFY^1CF_2)_nOCF=CF_2$ wherein $X^1$ is a halogen atom, $Y^1$ is a fluorine atom or a trifluoromethyl group, m is an integer of 0 to 5, and n is an integer of 0 to 2;
and

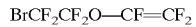

$BrCF_2CF_2O-CF=CF_2$

In addition to the above-exemplified fluoroelastomers, the following hydrocarbon elastomers may be exemplified as peroxide-curable elastomers:

acrylic rubbers, natural rubbers, synthetic rubbers, ethylene-propylene rubbers, ethylene-propylene-third diene rubbers, butadiene-styrene rubbers, polybutadiene rubbers, halogenated butyl rubbers, chloroprene rubbers, isobutylene-isoprene rubbers, butadiene-acrylonitrile rubbers, chlorosulfonated polyethylene rubbers, epichlorohydrine rubbers, and epichlorohydrine-ethylene oxide rubbers.

The acrylic rubbers will be explained in detail.

A peroxide-curable acrylic rubber may be prepared by copolymerizing the combination of the following (meth) acrylate ester monomer and the following polyfunctional monomer by any conventional polymerization method.

A (meth)acrylate ester monomer is represented by the formula:

$CH_2=C(R^1)COOR^2$ wherein $R^1$ is a hydrogen atom or a methyl group, and $R^2$ is a $C_1$–$C_8$ alkyl group which may be substituted with an alkoxy group. Specific examples of such an ester are methyl (meth)acrylate, ethyl (meth)acrylate, propyl (meth)acrylate, butyl (meth)acrylate, pentyl (meth)acrylate, hexyl (meth) acrylate, heptyl (meth)acrylate, octyl (meth)acrylate, 2-ethylhexyl (meth)acrylate, methoxyethyl (meth)acrylate, ethoxyethyl (meth)acrylate, and the like.

Specific examples of the polyfunctional monomer are ethylene glycol di(meth)acrylate, 1,4-butanediol di (meth) acrylate, 1,6-hexanediol di (meth) acrylate, polyethylene glycol di(meth)acrylate, allyl (meth)acrylate, divinylbenzene, triallyl cyanurate, triallyl isocyanurate, and the like. Among them, difunctional monomers are preferable since it is difficult to control the degree of partial crosslinking in the course of polymerization when a monomer having three or more functionalities is used.

The amount of the polyfunctional monomer is from 0.1 to 5 wt. %, preferably from 0.1 to 1.5 wt. %, in particular from 0.3 to 0.7 wt. %, based on the total weight of the (meth) acrylate ester monomer and the polyfunctional monomer. When the amount of the polyfunctional monomer is too low, the acrylic rubber is insufficiently crosslinked and thus the molding of the rubber becomes difficult. In addition, a cured material has low heat resistance or poor mechanical properties. When the amount of the polyfunctional monomer is too high, the degree of partial crosslinking increases and thus the processability deteriorates. Furthermore, a cured material loses flexibility and has decreased elongation, since a crosslinking degree after curing becomes too high. Thus, such a cured material cannot be used as a sealing material, and the like.

For the modification of an acrylic rubber, a part of the (meth) acrylate ester monomer may be replaced with an ethylenically unsaturated monomer such as acrylonitrile, styrene, vinyl acetate, ethylene, vinyl chloride, etc. The amount of such an ethylenically unsaturated monomer is preferably 40 wt. % or less of the (meth)acrylate ester monomer.

An acrylic rubber may have crosslinking sites consisting of halogen atoms such as iodine atoms or bromine atoms. For example, such an acrylic rubber can be prepared by copolymerizing an acrylic crosslinking-site monomer of the following formula (1), (2) or (3) and an acrylic monomer of the following formula (4):

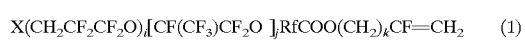

$X(CH_2CF_2CF_2O)_i[CF(CF_3)CF_2O]_jRfCOO(CH_2)_kCF=CH_2$    (1)

wherein X is I or Br, i is a number of 0 to 2, j is a number of 0 to 2, k is a number of 0 to 2, and Rf is —$CF(CF_3)$— or —$CH_2CF_2$—;

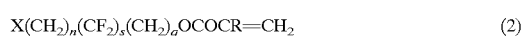

$X(CH_2)_n(CF_2)_s(CH_2)_qOCOCR=CH_2$    (2)

wherein X is I or Br, R is H, F or $CH_3$, n is a number of 0 to 3, s is a number of 0 to 4, q is a number of 0 to 2, and the sum of n and q is at least 1:

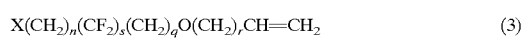

$X(CH_2)_n(CF_2)_s(CH_2)_qO(CH_2)_rCH=CH_2$    (3)

wherein X is I or Br, n is a number of 0 to 3, s is a number of 0 to 4, q is a number of 0 to 2, r is a number of 0 to 2, and the sum of n and q is at least 1;

$CH_2=C(R^1)COOR^2$    (4)

wherein $R^1$ is H, F or $CH_3$, $R^2$ is a $C_1$–$C_8$ alkyl group, an alkoxyalkyl group having the total number of carbon atoms of from 1 to 8 in the alkoxy and alkyl groups, or a $C_1$–$C_9$ fluoroalkyl group of the formula: —$CH_2(CF_2)_tY$ in which t is an integer of 1 to 8 and Y is H or F.

Specific examples of the monomer of the formula (1) are $ICH_2CF_2COOCH_2CH=CH_2$, $BrCH_2CF_2COOCH_2CH=CH_2$, $ICH_2CF_2CF_2OCF(CF_3)CF_2O—CF(CF_3)COOCH=CH_2$, and the like.

Specific examples of the monomer of the formula (2) are $ICF_2CF_2CF_2CF_2CH_2CH_2OCOCH=CH_2$, $BrCF_2CF_2CF_2CF_2CH_2CH_2OCOCH=CH_2$, $ICF_2CF_2CH_2CH_2OCOCH=CH_2$, $ICH_2CH_2OCOCF=CH_2$, $ICH_2CH_2OCOCH=CH_2$, and the like.

Specific examples of the monomer of the formula (3) are $ICF_2CF_2CF_2CF_2CH_2CH_2OCH_2CH=CH_2$, $BrCF_2CF_2CF_2CF_2CH_2CH_2OCH_2CH=CH_2$, $ICH_2CH_2OCH_2CH=CH_2$, and the like.

Specific examples of the acrylic monomer of the formula (4) are methyl acrylate, ethyl acrylate, propyl acrylate, butyl acrylate, 2-methoxyethyl acrylate, 2-ethoxyethyl acrylate, pentafluoropropyl acrylate, tetrafluoropropyl acrylate, octafluoropentyl acrylate, and corresponding methacrylates and α-fluoroacrylates.

The amount of such a monomer containing an iodine or bromine atom is selected such that the amount of iodine or bromine atoms in the obtained acrylic elastomer is from 0.01 to 10 wt. %, preferably from 0.1 to 3 wt. %. When the amount of iodine or bromine atoms in the acrylic elastomer is less than 0.01 wt. %, the crosslinking is insufficient, and thus the obtained acrylic elastomer has low tensile strength. When the amount of iodine or bromine atoms exceeds 10 wt. %, the crosslinking is excessive, and thus the elastomer is insufficiently elongated.

Other copolymerizable monomer may be copolymerized instead of the acrylate, methacrylate or α-fluoroacrylate monomer. The amount of the other copolymerizable monomer does not exceed about 30 mole %. Examples of the other copolymerizable monomer are ethylene, propylene, vinyl chloride, vinylidene chloride, acrylonitrile, vinyl acetate, ethyl vinyl ether, butyl vinyl ether, styrene, and the like.

The Mooney viscosity $ML_{1+10}100°$ C. of the acrylic elastomer is preferably from 10 to 150, and the molecular weight of the acrylic elastomer is preferably from about 30,000 to 2,000,000.

A peroxide-curable elastomer may be a blend of an above-described fluoroelastomer and a hydrocarbon elastomer.

Peroxides which are used to cure such an elastomer are preferably organic peroxides. The organic peroxide is usually used in an amount of 0.05 to 10 wt. parts per 100 wt. parts of an elastomer.

Organic peroxides, which easily generate peroxy radicals in the presence of heat or a redox system, are preferably used. Preferable examples of organic peroxides are 3,5-dimethyl-2,5-di-tert.-butylperoxyhexane (Perhexa 2,5B), 1,1-bis(tert.-butylperoxy)-3,5,5-trimethylcyclohexane, 2,5-dimethylhexane-2,5-dihydroperoxide, di-tert.-butyl peroxide, tert.-butylcumyl peroxide, dicumyl peroxide, α,α'-bis(tert.-butylperoxy)-p-diisopropylbenzene, 2,5-dimethyl-2,5-di(tert.-butylperoxy)hexane, 2,5-dimethyl-2,5-di(tert.-butylperoxy)hexyne-3, benzoyl peroxide, tert.-butylperoxybenzene, 2,5-dimethyl-2,5-di(benzoylperoxy)hexane, tert.-butyl peroxymaleate, tert.-butylperoxyisopropyl carbonate, and the like. Among them, dialkyl type ones are more preferable. In general, the kind and amount of the peroxide are selected by taking into account the amount of active —O—O—, the decomposition temperature of the peroxide, etc.

A fluorine-containing triallyl isocyanurate as a crosslinking aid is used in an amount of from 0.1 to 10 wt. parts, preferably from to 10 wt. parts, per 100 wt. parts of an elastomer. If desired, other crosslinking aid comprising a conventional polyfunctional unsaturated hydrocarbon compound such as triallyl isocyanurate may be used in combination with a fluorine-containing triallyl isocyanurate. The combined use of crosslinking aids can provide a curable composition which has an unexpectedly increased curing rate while maintaining heat resistance of a cured material.

Such a polyfunctional unsaturated hydrocarbon compound may be any compound which is copolymerizable with the above fluorine-containing triallyl isocyanurate. Examples of such a polyfunctional unsaturated hydrocarbon compound are as follows:

triallyl cyanurate, triallyl isocyanurate, triallyl formal, triallyl trimellitate, dipropargyl terephthalate, diallyl phthalate, tetraallyl terephthalamide, triallyl phosphate. Among them, triallyl isocyanurate is preferable.

The amounts of a fluorine-containing triallyl isocyanurate and a fluorine-free polyfunctional unsaturated hydrocarbon compound are preferably 1 to 99 wt. parts of the former and 99 to 1 wt. parts of the latter, more preferably 10 to 99 wt. parts of the former and 90 to 1 wt. parts of the latter. As the amount of the fluorine-containing triallyl isocyanurate increases, the heat resistance increases.

Furthermore, the curable composition of the present invention may optionally contain fillers, processing aids, antioxidants, anti-aging agents, antiozonants, UV-ray absorbers, and the like.

Examples of the fillers include metal oxides (e.g. magnesium oxide, calcium oxide, titanium oxide, silicon oxide, aluminum oxide, etc.), metal hydroxides (e.g. magnesium hydroxide, aluminum hydroxide, calcium hydroxide, etc.), carbonates (e.g. magnesium carbonate, aluminum carbonate, calcium carbonate, barium carbonate, etc.), silicates (e.g. magnesium silicate, calcium silicate, sodium silicate, aluminum silicate, etc.), sulfates (e.g. aluminum sulfate, calcium sulfate, barium sulfate, etc.), metal sulfides (e.g. synthetic hydrotalcites, molybdenum disulfide, iron sulfide, copper sulfide, etc.), diatomaceous earth, asbestos, lithopone (zinc sulfide/barium sulfide), graphite, carbon black, carbon fluoride, calcium fluoride, cokes, and the like.

Examples of the processing aids are higher fatty acids (e.g. stearic acid, oleic acid, palmitic acid, lauric acid, etc.), higher fatty acid salts (e.g. sodium stearate, zinc stearate, etc.), higher fatty acid amides (e.g. stearylamide, oleylamide, etc.), higher fatty acid esters (e.g. ethyl oleate, etc.), higher fatty acid amines (e.g. stearylamine, oleylamine, etc.), waxes (e.g. carnauba wax, ceresin wax, etc.), polyglycols, (e.g. ethylene glycol, grycerol, diethylene glycol, etc.), aliphatic hydrocarbons (e.g. Vaseline, paraffins, etc.), silicone oils, silicone polymers, low molecular weight polyethylene, phthalate esters, phosphate esters, rosin, (halogenated) dialkylamine, (halogenated) dialkylsulfone, surfactants, and the like.

Examples of the antioxidants, anti-aging agents and ozonants include phenol compounds (e.g. 2,5-di-tert.-amylhydroquinone, etc.), amine-ketone compounds (e.g. 2,2,4-trimethyl-1,2-dihydroquinoline, etc.), secondary aromatic amines (e.g. 4,4'-bis(α,α-dimethylbenzyl)diphenylamine, etc.), and the like.

Examples of the UV-ray absorbers include benzophenone compounds (e.g. 2,4-dihydroxybenzophenone, etc.), amines (e.g. bis(2,2,6,6-tetramethyl-4-piperidyl) sebacate, etc.), benzotriazole compounds (e.g. 2-(2'-hydroxy-5'-methylphenyl)benzotriazole, etc.), and the like.

When an elastomer is cured with a peroxide in the presence of a crosslinking aid comprising a fluorine-containing triallyl isocyanurate of the present invention, curing processes and conditions are as follows:

Suitable mixing methods are employed in accordance with the viscoelasticity and forms of components. For example, components are kneaded with conventional open rolls, powder mixer, etc. or co-coagulated from a mixture of emulsions of the components. Solid components may be dissolved or dispersed in a solvent, and then mixed.

Molding methods may be any conventional molding methods, for example, compression molding, extrusion molding, injection molding, transfer molding, etc.

A curing temperature and a curing time depend on the kind of an organic peroxide to be used. In general, press-curing (primary curing) is carried out at a temperature of from 120 to 200° C. for 5 to 30 minutes, and oven-curing (secondary curing) is carried out at a temperature of from 150 to 300° C., preferably from 150 to 250° C. for 1 to 24 hours. When a composition is cured at a relatively high temperature, for example, 200° C. or higher, oxidative degradation can be prevented by carrying out the curing under the atmosphere of an inert gas such as nitrogen gas.

A crosslinking aid comprising the fluorine-containing triallyl isocyanurate of the present invention exhibits good curing properties, and obtained cured materials have excellent mechanical properties and heat resistance, even when it is used as a crosslinking aid for elastomers which are required to have good heat resistance, in particular, fluororubbers.

Applications of cured materials are listed below:

Automobile fields: fuel hoses, fuel pump diaphragm, crankshaft seals, valve stem seals, bearing seals, EGR hoses, CAC valves, needle tips, electric wires around engines, O-rings of fuel-injection equipment, filler hoses, O-rings of automobile air conditioners, intake gaskets;

Office automation fields: cleaning blades of copying machines, rolls of copying machines, gaskets of computers, cooling hoses of mainframes;

Electric fields: caps for insulating oils, venting seals of liquid-seal type transformers, jackets of oil well cables, oil- and heat-resistant electric wires;

Chemical/mechanical fields: O-rings of chemical pumps, seals of chemical pumps, flow-meters and pipes, seals of heat exchangers, packings of high-temperature vacuum driers, dyeing rolls, coatings of plating jigs, seals of hydraulic or lubricating machines, seals of dry-cleaning apparatuses, seals of automatic packaging machines, pinch rolls for pickling, cables of robots, solvent rolls, seals of apparatuses for the production of semiconductors;

Food/drug fields: sanitary pipe packing, jar and pot packing, packing of pressure cookers, electromagnetic valve seals for plate type heat exchangers and vending machines, seals of hot water heaters, tubes;

Ship/aircraft fields: seals of stern tubes, valve sheets of butterfly valves, fuel hoses, gaskets, rotating shaft seals, gaskets of hydraulic equipment, fire wall seals.

The present invention will be illustrated by the following Examples and Comparative Examples.

EXAMPLE 1

Synthesis of 1,3,5-tris(2,3,3-trifluoro-2-propenyl)-1,3,5-triazine-2,4,6-trione $HCF_2CF_2CH_2OH \longrightarrow CF_2=CFCH_2OH \longrightarrow$

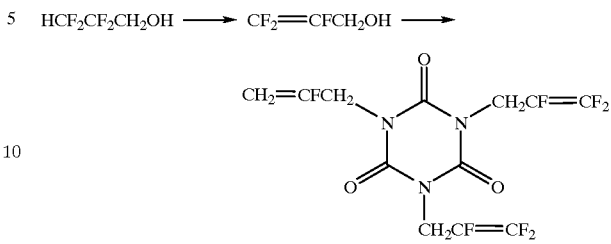

According to the method described by Nguyen, T. et al, in J. Org. Chem., 54(23), 5640–5642 (1989), a mixture of 2,2,3,3-tetrafluoro-1-propanol (75 g, 0.57 mole) and diethyl ether (75ml) was cooled to 0° C., and then mixed and reacted with the 1.4 M solution of methyl lithium in diethyl ether (800 ml) (1.12 moles of methyl lithium) to obtain 2,3,3-trifluoroallyl alcohol (20.5 g, 0.18 mole), which was used in the subsequent reaction.

2,3,3-Trifluoroallyl alcohol (39.8 g, 0.353 mole), triphenylphosphine (140 g, 0.533 mole), cyanuric acid (11.4 g, 0.0883 mole) and dimethylacetamide (800 ml) were mixed. To the stirred mixture, the 40% solution of diethyl azodicarboxylate in toluene (0.528 mole) was slowly dropwise added so that the reaction temperature did not exceed 30° C. After the addition, the mixture was stirred overnight at room temperature. After the termination of the reaction, the solvent was evaporated off under reduced pressure.

The resulting concentrated mixture was purified by silica gel chromatography [Column: SILICA GEL 60 (available from Merk) packed column; eluent:n-hexane-toluene (volume ratio of 1:4)]. Fractions containing the above-entitled compound were combined and concentrated. To the concentrate, diethyl ether was added, and the formed precipitate was filtrated with suction and then thoroughly washed with diethyl ether. The filtrate was concentrated, and the obtained concentrate was again purified by silica gel chromatography (under the same conditions as above). The obtained compound was recrystallized from diethyl ether-n-hexane to obtain the entitled compound (14.4 g, 0.035 mole).

$^1$H-NMR (CDCl$_3$) δ: 4.82 (2H, ddd, J=18.6, 3.3, 2.4 Hz).

$^{19}$F-NMR (CDCl$_3$) δ: −98.7 (1F, ddt, J=68.7, 33.9, 2.4 Hz), −116.41 (1F, ddt, J=114.7, 68.7, 3.3 Hz), −180.12 (1F, ddt, J=114.7, 33.9, 18.6 Hz).

IR (KBr): 3024, 1804, 1704, 1450, 1176, 979.

EXAMPLE 2

Synthesis of 1,3,5-tris(2,3-difluoro-2-propenyl)-1,3,5-triazine-2,4,6-trione

Methyl lithium (1.06 M solution in ether) (175 ml) was dropwise added to the solution of trifluoroallyl alcohol (18.3 g) in diethyl ether (400 ml) at 0° C. over one hour. After 15 minutes, lithium aluminum hydride (6.2 g) was added portion by portion. A reactor was immersed in an oil bath (40° C.), and the content was refluxed for 1.5 hours. The reaction mixture was again cooled to 0° C., and water (24 ml) and the 15% aqueous solution of sodium hydroxide (7 ml) were calmly added to the reaction mixture, followed by drying over magnesium sulfate. After filtration, the solvent was removed, and 2,3-difluoroallyl alcohol (9.5 g) was recovered by distillation under atmospheric pressure.

$^1$H-NMR δ: 1.96 (1H, t, J=6.5 Hz), 4.40 (2H, ddd, J=21.8, 6.5, 5.3 Hz), 7.08 (1H, dd, J=76.0, 2.9 Hz).

$^{19}$F-NMR (CDCl$_3$) δ: −167.7 (1F, ddt, J=129.7, 2.9, 21.8 Hz), 178.5 (1F, ddt, J=129.7, 76.0, 5.3 Hz).

Diethyl azodicarboxylate (40% solution in toluene) (35 ml) was dropwise added at room temperature to the solution of 2,3-difluoroallyl alcohol (6.74 g), cyanuric acid (2.64 g) and triphenylphosphine (21.5 g) in dimethylacetamide (150 ml), followed by stirring for 2 hours. The solvent was evaporated off under reduced pressure, and the residue was purified by silica gel chromatography [a medium pressure column: ULTRAPACK ST-40 (available from YAMAZEN); pressure: about 4 kgf; eluent: n-hexane-ethyl acetate (volume ratio of 15:1)] to obtain the above-entitled compound (1.27 g). The purity was over 98%.

$^1$H-NMR δ: 4.90 (2H, dd, J=16.1, 4.0 Hz), 7.18 (1H, dd, J=74.5, 3.0 Hz).

$^{19}$F-NMR δ: −167.24 (1F, ddt, J=130.1, 3.0, 16.1 Hz), −176.35 (1F, ddt, J=130.1 74.5, 4.0 Hz).

REFERENCE EXAMPLE

Synthesis of 1,3,5-tris(3-fluoro-2-propenyl)-1,3,5-triazine-2,4,6-trione

The mixture of allyl bromide (1.0 ml), N-bromosuccinimide (6.0 g), 2,2'-azobisisobutyronitirle (50 mg) and benzene (10 ml) was charged in a stainless steel autoclave, and heated at 80° C. for 20 hours while stirring. After cooling, the autoclave was opened in an air, and the reaction mixture was filtrated to remove insoluble materials. The filtrate was distilled under atmospheric pressure, and distillates distilled at 80° C. or less (including benzene) were collected, and used in the subsequent reaction.

The mixture of the distillates (benzene solutions) collected in the previous step, trisodium cuanurate (200 mg) and dimethylacetamide (10 ml) was heated at 80° C. for 24 hours while stirring. After evaporating off the solvent under reduced pressure, the residue was poured in the mixture of diethyl ether and water (volume ratio of 1:1), and extracted with diethyl ether (30 ml) three times. The ether layers were combined, and washed with saturated saline, followed by drying over magnesium sulfate. After evaporating off the solvent, the residue was purified by silica gel chromatography [Column: SILICA GEL 60 (available from Merk) packed column; eluent: n-hexane-ethyl acetate (volume ratio of 3:1] to obtain the above-entitled compound (205 mg). Yield: 66%.

$^1$H-NMR (CDCl$_3$) ∂: 4.36–4.42 (m, 6/5H), 4.59–4.65 (m, 4/5H), 4.81–5.11 (m, 2/5H), 5.40–5.63 (m, 3/5H), 6.35–6.80 (m, 2/5H), 6.63–7.12 (m, 3/5H).

$^{19}$F-NMR (CDCl$_3$) δ: −121.66−−122.38 (m, 3/5H), −124.52−−125.20 (m, 2/5H).

IR (KBr): 1681, 1455, 1114, 923 cm$^{-1}$.

EXAMPLE 3

Homopolymerization of 1,3,5-tris(2,3,3-trifluoro-2-propenyl)-1,3,5-triazine-2,4,6-trione 1,3,5-Tris(2,3,3-trifluoro-2-propenyl)-1,3,5-triazine-2,4,6-trione (82.2 mg, 0.2 mmol), which was obtained in Example 1, and Perhexa 2.5B (3,5-dimethyl-2,5-di-tert.-butylperoxyhexane) (87 mg, 0.3 mmol) were charged in a sample bottle, and the bottle was capped. Then, the sample bottle was placed in an oven at 170° C. After 2 minutes, the content polymerized, and a white solid formed. This period of time was assumed as a polymerization time. The sample bottle was further kept in the oven. After 10 minutes, the sample bottle was removed from the oven and cooled.

The heat resistance of the obtained polymer was evaluated with TG/DTA (RTG 220 manufactured by SEIKO ELECTRONICS Co., Ltd.) The decomposition temperature was 320° C. The measurement was carried out in an air stream of 200 ml/min. by heating a sample from 20° C. to 600° C. at a heating rate of 10° C./min., and a temperature at which the weight loss of the polymer reached 10% was regarded as a decomposition temperature.

EXAMPLE 4

Homopolymerization of 1,3,5-tris(2,3-difluoro-2-propenyl)-1,3,5-triazine-2,4,6-trione Polymerization was carried out in the same manner as in Example 3 except that 1,3,5-tris(2,3-difluoro-2-propenyl)-1,3,5-triazine-2,4,6-trione (71.4 mg, 0.2 mmol), which had been synthesized in Example 2, was used in place of 1,3,5-tris(2,3,3-trifluoro-2-propenyl)-1,3,5-triazine-2,4,6-trione. a polymerization time was 2 minutes, and A decomposition temperature was 380° C.

COMPARATIVE EXAMPLE 1

Homopolymerization of triallyl isocyanurate

Polymerization was carried out in the same manner as in Example 3 except that triallyl isocyanurate (49.9 mg, 0.2 mmol) was used in place of 1,3,5-tris(2,3,3-trifluoro-2-propenyl)-1,3,5-triazine-2,4,6-trione. A polymerization time was 1 minute, and a decomposition temperature was 270° C.

COMPARATIVE EXAMPLE 2

Homopolyumerization of 1,3,5-tris(2-fluoro-2-propenyl)-1,3,5-triazine-2,4,6-trione Polymerization was carried out in the same manner as in Example 3 except that 1,3,5-tris(2-fluoro-2-propenyl)-1,3,5-triazine-2,4,6-trione (60.6 mg mg, 0.2 mmol), which had been synthesized by a known method, was used in place of 1,3,5-tris(2,3,3-trifluoro-2-propenyl)-1,3,5-triazine-2,4,6-trione. A polymerization time was 1 minute, and a decomposition temperature was 120° C.

COMPARATIVE EXAMPLE 3

Homopolymerization of 1,3,5-tris(3,3-difluoro-2-propenyl)-1,3,5-triazine-2,4,6-trione Polymerization was carried out in the same manner as in Example 3 except that 1,3,5-tris(3,3-difluoro-2-propenyl)-1,3,5-triazine-2,4,6-trione (71.4mg mg, 0.2 mmol), which had been synthesized by a known method, was used in place of 1,3,5-tris(2,3,3-trifluoro-2-propenyl)-1,3,5-triazine-2,4,6-trione. A polymerization time was 5 minutes, and a decomposition temperature was 110° C.

COMPARATIVE EXAMPLE 4

Homopolymerization of 1,3,5-tris(3-fluoro-2-propenyl)-1,3,5-triazine-2,4,6-trione Polymerization was carried out in the same manner as in Example 3 except that 1,3,5-tris(3-fluoro-2-propenyl)-1,3,5-triazine-2,4,6-trione (60.6 mg mg, 0.2 mmol), which had been synthesized in Reference Example, was used in place of 1,3,5-tris(2,3,3-trifluoro-2-propenyl)-1,3,5-triazine-2,4,6-trione. A polymerization temperature was 2 minutes, and a decomposition temperature was 105° C.

EXAMPLES 5–7 AND COMPARATIVE EXAMPLES 5–6

Curing of a fluororubber using a fluorine-containing triallyl isocyanurate

The components, which were compounded according to the formulation in Table 1, was kneaded with 8 inch rolls to prepare a curable composition, and curing properties of the composition were measured at 160° C. with a Curastometer (JIS II type).

The composition was cured by press curing at 160° C. for 30 minutes and then oven curing at 180° C. for 4 hours, and properties of the cured material were measured. The measurement of the properties of the cured material, aging tests, and the measurement of compression set were carried out according to JIS K 6301

The results are shown in Table 1, in which "parts" are "parts by weight".

Polymer A was a perfluoroelastomer, which was prepared by copolymerizing tetralfuoroethylene, perfluoro(methyl vinyl ether) and 1,1,2,2-tetrafluoro-3-iodopropyl trifluorovinyl ether in a molar ratio of 59.9:39.8:0.3 in the presence of 1,4-diiodoperfluorobutane, and had a Mooney viscosity ($ML_{1+10}100°$ C.) of 69, and an iodine content of 0.3 wt. %.

DAIEL G-902 is a vinylidene fluoride-tetrafluoroethylene-hexafluoropropylene copolymeric fluororubber (available from DAIKIN Industries, Ltd.).

The numerals in the parentheses in the results in the aging test are percentages (%) of changes from the dry properties.

EXAMPLES 8–10 AND COMPARATIVE EXAMPLE 7

Curing of a fluororubber using a fluorine-containing triallyl isocyanurate

The components, which were compounded according to the formulation in Table 2, was kneaded with 8 inch rolls to prepare a curable composition, and curing properties of the composition were measured at 160° C. with a Curastometer (JIS II type).

The composition was cured by press curing at 140° C. for 15 minutes (Example 8) or at 160° C. for 10 minutes (Examples 9–10 and Comparative Example 7) and then oven curing at 230° C. for 24 hours, and properties of the cured

TABLE 1

|  | Ex. 5 | Ex. 6 | C. Ex. 5 | C. Ex. 6 | Ex. 7 |
| --- | --- | --- | --- | --- | --- |
| <Formulation> |  |  |  |  |  |
| Polymer A | 100 | 100 | 100 |  |  |
| DAIEL G-902 |  |  |  | 100 | 100 |
| MT-C[1] | 20 | 20 | 20 | 20 | 20 |
| Perhexa 2.5B | 4 | 4 | 1.5 | 1.5 | 1.5 |
| F-TAIC[2] | 4 | 6 | — | — | 4 |
| TAIC[3]3 | — | — | 4 | 4 | 1 |
| <Curing properties> 160° C., Curastometer II |  |  |  |  |  |
| ML[4] (kgf) | 0.06 | 0.06 | 0.10 | 0.05 | 0.55 |
| MH[5] (kgf) | 3.17 | 2.50 | 7.30 | 5.50 | 3.55 |
| $T_{10}$[6] (min.) | 1.7 | 1.6 | 0.6 | 0.9 | 0.8 |
| $T_{90}$[7] (min.) | 9.5 | 12.0 | 1.4 | 2.2 | 3.8 |
| <Curing conditions> |  |  |  |  |  |
| Press curing | 160° C. × 30 minutes |  |  |  |  |
| Oven curing | 180° C. × 4 hours |  |  |  |  |
| <Dry properties> Oven 180° C. × 4 hours |  |  |  |  |  |
| $M_{100}$[8] | 120 | 142 | 137 | 31 | 23 |
| $T_b$[9] | 179 | 189 | 191 | 226 | 204 |
| $E_b$[10] | 150 | 130 | 300 | 300 | 360 |
| Hs[11] | 82 | 83 | 86 | 70 | 70 |
| <Aging test> 250° C. × 70 hours |  |  |  |  |  |
| $M_{100}$ | 91 (−24) | 100 (−30) | 89 (−35) | 21 (−32) | 22 (−4) |
| $T_b$ | 159 (−11) | 190 (+1) | 154 (−19) | 86 (−62) | 165 (−19) |
| $E_b$ | 170 (+13) | 180 (+38) | 220 (+69) | 560 (+87) | 500 (+39) |
| Hs | 81 (−1) | 82 (−1) | 84 (−2) | 71 (+1) | 70 (0) |
| <Compression set> P-24 O-ring |  |  |  |  |  |
| 200° C. × 70 hrs | 40.2% | 14.8% | 12.4% | 31.2% | 22.4% |

Notes:
[1])Medium thermal carbon black ("N-990" manufactured by CANCARB Ltd.)
[2])1,3,5-Tris(2,3,3-trifluoro-2-propenyl)-1,3,5-triazine-2,4,6-trione.
[3])Triallyl isocyanurate.
[4])ML: Lowest viscosity (unit: kgf).
[5])MH: Curing degree (unit: kgf)
[6])$T_{10}$: Induction time (unit: minutes)
[7])$T_{90}$: Optimum curing time (unit: minutes).
[8])$M_{100}$: 100% modulus (unit: $kgf/cm^2$).
[9])$T_b$: Tensile strength at break (unit: $kgf/cm^2$).
[10])$E_b$: Elongation at break (unit: %).
[11])Hs: JIS A hardness.

In Table 1, "Oven 180° C.×4 hours" means that the properties were measured after oven-curing at 180° C. for 4 hours.

material were measured. The measurement of the properties of the cured material, aging tests, and the measurement of compression set were carried out according to JIS K 6301

The results are shown in Table 2, in which "parts" are "parts by weight".

TABLE 2

|  | Ex. 8 | Ex. 9 | Ex. 10 | C. Ex. 7 |
|---|---|---|---|---|
| <Formulation> | | | | |
| Polymer A DAIEL G-902 | 100 | 100 | 100 | 100 |
| MT-C[1)] | 20 | 20 | 20 | 20 |
| Perhexa 2.5B | 4 | 4 | 4 | 4 |
| F-TAIC[2)] | 6 | 2 | 1 | 0 |
| TAIC[3)] | 1 | 1 | 1 | 1 |
| <Curing properties> Curastometer II | | | | |
|  | (140° C.) (160° C.) | (160° C.) | (160° C.) | (160° C.) |
| $ML^{4)}$ (kgf) | 0.12  0.2 | 0.11 | 0.09 | 0.09 |
| $MH^{5)}$ (kgf) | 5.27  8.9 | 5.94 | 5.84 | 5.77 |
| $T_{10}^{6)}$ (min.) | 0.89  0.32 | 0.61 | 0.62 | 0.59 |
| $T_{90}^{7)}$ (min.) | 2.06  1.25 | 1.80 | 1.62 | 1.60 |
| <Curing conditions> | | | | |
| Press curing | 140° C. × 15 min. | 160° C. × 30 min. | | |
| Oven curing | 230° C. × 24 hours | | | |
| <Dry properties> Oven 230° C. × 24 hours | | | | |
| $M_{100}^{8)}$ | 139 | 111 | 101 | 84 |
| $T_b^{9)}$ | 209 | 209 | 218 | 211 |
| $E_b^{10)}$ | 160 | 110 | 170 | 190 |
| $Hs^{11)}$ | 87 | 79 | 78 | 78 |
| <Aging test> 250° C. × 70 hours | | | | |
| $M_{100}$ | 116 (−17) | | | |
| $T_b$ | 178 (−15) | | | |
| $E_b$ | 170 (+8) | | | |
| Hs | 85 (−2) | | | |
| <Compression set> P-24 O-ring | | | | |
| 200° C. × 70 hrs | 14.5% | 11.6% | 10.8% | 16.2% |
| 200° C. × 600 hrs | 34.7% | 26.3% | 32.4% | 53.0% |

Notes: [1)–11)] See the Notes for Table 1.

What is claimed is:

1. A fluorine-containing trialyl isocyanurate of the formula (I):

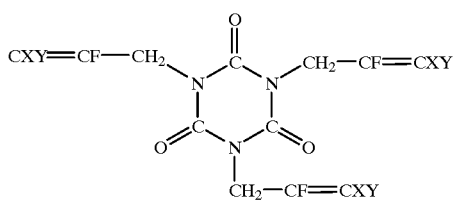

[I]

wherein at least one of X and Y is a fluorine atom, and the other is a hydrogen atom or a fluorine atom.

2. A crosslinking aid comprising a fluorine-containing triallyl isocyanurate of the formula (II):

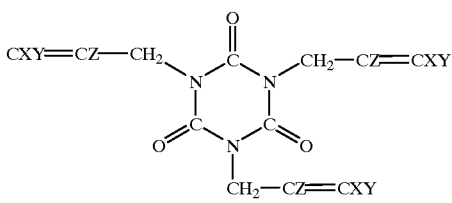

[II]

wherein at least one of X, Y and Z is a fluorine atom, and the others are hydrogen or fluorine atoms, with the proviso that if Z is a hydrogen atom then X and Y are not both fluorine atoms.

3. A crosslinking aid comprising a fluorine-containing triallyl isocyanurate of the formula (I):

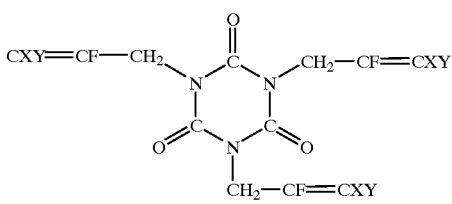

[I]

wherein at least one of X and Y is a fluorine atom, and the other is a hydrogen atom or fluorine atom.

4. A crosslinking aid composition comprising a fluorine-containing triallyl isocyanurate as claimed in claim 2, and a polyfunctional unsaturated hydrocarbon compound.

5. A crosslinking aid composition according to claim 4, which comprises 1 to 99 wt. parts of said fluorine-containing triallyl isocyanurates, and 99 to 1 wt. parts of said polyfunctional unsaturated hydrocarbon compound.

6. A crosslinking aid composition according to claim 4, which comprises 10 to 99 wt. parts of said fluorine-containing triallyl isocyanurate, and 90 to 10 wt. parts of said polyfunctional unsaturated hydrocarbon compound.

7. A crosslinking aid composition according to claim 4, wherein said polyfunctional unsaturated hydrocarbon compound is triallyl isocyanurate.

8. A curable elastomer composition comprising a peroxide-curable elastomer, a crosslinking aid as claimed in claim 2, and an organic peroxide.

9. A curable elastomer composition comprising a peroxide-curable elastomer, a crosslinking aid as claimed in claim 3, and an organic peroxide.

10. A curable elastomer composition comprising a peroxide-curable elastomer, a crosslinking aid composition as claimed in claim 4, and an organic peroxide.

11. A curable elastomer composition according to claim 8, 9 or 10, wherein said peroxide-curable elastomer is a fluoroelastomer.

12. A curable elastomer composition according to claim 11, which contains no acid-scavenger.

13. A method for the curing of a peroxide-curable elastomer comprising curing said elastomer with an organic peroxide in the presence of a crosslinking aid as claimed in claim 2.

14. A method for the curing of a peroxide-curable elastomer comprising curing said elastomer with an organic peroxide in the presence of a crosslinking aid as claimed in claim 3.

15. A method for the curing of a peroxide-curable elastomer comprising curing said elastomer with an organic peroxide in the presence of a crosslinking aid composition as claimed in claim 4.

16. A shaped article which is obtained by shaping a curable elastomer composition as claimed claim 8 by compression molding, extrusion molding, transfer molding or injection molding, and optionally curing it second.

17. A sealing material which is obtained by shaping a curable elastomer composition as claimed in claim 8 by compression molding, extrusion molding, transfer molding or injection molding, and optionally curing it second.

18. A method for the curing of a peroxide-curable elastomer comprising curing said elastomer with an organic peroxide in the presence of a crosslinking aid comprising a fluorine-containing triallyl isocyanurate of the formula (II):

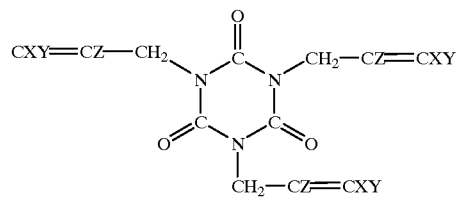

[II]

wherein at least one of X, Y and Z is a fluorine atom, and the others are hydrogen or fluorine atoms.

* * * * *